United States Patent [19]

Seki et al.

[11] 4,256,744
[45] Mar. 17, 1981

[54] AGRICULTURAL AND HORTICULTURAL PESTICIDES

[75] Inventors: Shigeo Seki; Yashuharu Sekizawa, both of Tokyo; Fumio Kai; Yukio Suzuki, both of Fujisawa; Michiaki Iwata; Tetsuro Watanabe, both of Yokohama, all of Japan

[73] Assignee: Meiji Seika Kaisha, Ltd., Tokyo, Japan

[21] Appl. No.: 9,028

[22] Filed: Feb. 2, 1979

[30] Foreign Application Priority Data

Feb. 14, 1978 [JP] Japan .................................. 53-14964
Feb. 14, 1978 [JP] Japan .................................. 53-14965

[51] Int. Cl.³ .......................................... C07D 277/62
[52] U.S. Cl. .............................. 424/248.51; 424/256; 424/274; 542/416; 548/208; 546/198; 544/133; 544/135
[58] Field of Search ................ 544/133, 135; 260/301; 424/143.8, 270, 248.51, 256, 274; 542/416; 548/208; 546/198

[56] References Cited
U.S. PATENT DOCUMENTS 3,284,450 11/1966 Kaaijeveld .......................... 260/243
3,539,584 11/1970 Suh ..................................... 260/304

*Primary Examiner*—Nicholas S. Rizzo
*Attorney, Agent, or Firm*—Sughrue, Rothwell, Mion, Zinn and Macpeak

[57] ABSTRACT

This invention relates to novel compounds of the general formula (I):

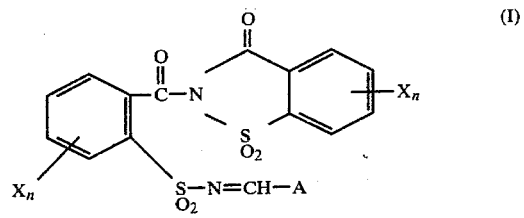

wherein A represents

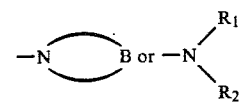

in which B represents a ring-forming residue of a 5- or 6-membered carbon-containing heterocycling ring containing at least one nitrogen atom and which may further contain an oxygen atom in the ring, and $R_1$ and $R_2$ are the same or different and each represents an alkyl group having from 1 to 6 carbon atoms, a phenyl group, a phenyl group substituted with an alkyl or alkoxy group having from 1 to 4 carbon atoms or a halogen atom, a benzyl group or a benzyl group substituted with an alkyl or alkoxy group having from 1 to 4 carbon atoms or a halogen atom; n represents 0 or an integer of from 1 to 4 corresponding to the number of X substituents; and X represents a halogen atom, a nitro group, a carboxyl group or a carbamoyl group and when two or more X substituents are present they may be the same or different; agents for controlling agricultural and horticultural plant diseases which contain these novel compounds as active ingredients; and to processes for preparing the novel compounds of formula (I).

28 Claims, No Drawings

AGRICULTURAL AND HORTICULTURAL PESTICIDES

BACKGROUND OF THE INVENTION

1. Field of the Invention

The present invention relates to agents for agricultural or horticultural use which prevent or restrain the growth of fungi and bacteria. More particularly, the present invention is directed to a group of compounds which are effective against rice blast.

2. Discussion of the Prior Art

Since 1,2-benzisothiazolin-3-one-1,1-dioxide derivatives were found to be useful as pesticidal agents for agricultural and horticultural plant diseases and to be particularly effective against rice blast, many related derivatives have been synthesized and tested. Above all, 3-allyloxy-1,2-benzoisothiazole-1,1-dioxide is gaining commercial acceptance as an anti-blast agent (Japanese Patent Publication Nos. 38080/70 and 37247/74).

The present inventors made various investigations regarding novel derivatives of compounds of this series. These investigations led to the discovery of the novel compounds of general formula (I) (to be referred to as "the compounds of this invention") which unexpectedly have superior anti-blast activity and anti-leaf blight activity and superior pesticidal and antimicrobial effects against vegetable diseases. The compounds of the present invention are a new type of agent which are effective against two of the three major rice diseases, i.e., blast, leaf blight and sheath blight, and are also effective against soft rot of Chinese cabbage, a serious vegetable disease, and which find a wide range of applications and a high level of safety not attainable heretofore.

SUMMARY OF THE INVENTION

A principal object of the present invention is to provide a novel group of compounds which are capable of preventing or inhibiting agricultural and horticultural diseases.

A more particular object of the present invention is to provide a novel group of compounds for agricultural and horticultural use which are capable of preventing or inhibiting the growth of fungi and bacteria.

Another object of the present invention is to provide a novel group of compounds which have superior anti-blast activity and anti-leaf blight activity and which are effective in controlling vegetable diseases.

A further object of the present invention is to provide a new type of agent which is effective against major rice diseases.

A final object of the present invention is to provide a composition for agricultural and horticultural use containing this class of compounds.

DETAILED DESCRIPTION OF THE INVENTION

The process for producing the compounds of this invention, the method of their application, the formulation of pesticidal agents, and the efficacy of such pesticidal agents will be described below in detail.

In the general formula (I) the heterocyclic ring B may be a 5- or 6-membered heterocyclic ring containing at least one nitrogen atom as the hetero atom. The heterocyclic ring may further contain an oxygen atom as a hetero atom. Examples of the heterocyclic ring include morpholine, piperidine, pyrrolidine, etc.

The alkyl group represented by $R_1$ and/or $R_2$ may be a straight chain, branched chain or cyclic alkyl group having 1 to 6 carbon atoms. Examples of the alkyl group include a methyl group, an ethyl group, an n-propyl group, an iso-propyl group, an n-butyl group, an iso-butyl group, a tert-butyl group, an iso-amyl group, an n-pentyl group, an n-hexyl group, etc. More preferable examples of the alkyl group are a methyl group and an ethyl group.

The aryl group represented by $R_1$ and/or $R_2$ may be a phenyl group or a substituted phenyl group wherein the substituent includes an alkyl group having 1 to 4 carbon atoms, an alkoxy group having 1 to 4 carbon atoms or a halogen atom. Preferably the aryl group is a phenyl group.

The aralkyl represented by $R_1$ and/or $R_2$ may be a benzyl group or a substituted benzyl group wherein the substituent includes an alkyl group having 1 to 4 carbon atoms, an alkoxy group having 1 to 4 carbon atoms or a halogen atom. A preferable aralkyl group is a benzyl group.

Of the halogen atoms represented by X a chlorine atom is preferable.

The compounds of this invention are synthesized by reacting compounds of general formula (II):

wherein A is as defined hereinabove, with compounds of general formula (III):

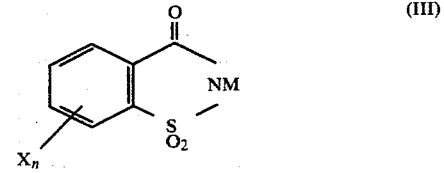

wherein n and X are as defined hereinabove and M represents a hydrogen atom or a monovalent cation, in the presence of acid condensing agents, i.e., reactive derivatives of an oxyacid at its hydroxyl group typified, for example, by inorganic or organic acid halides; anhydrides or mixed acid anhydrides or oxyacids. This reaction is schematically shown as follows:

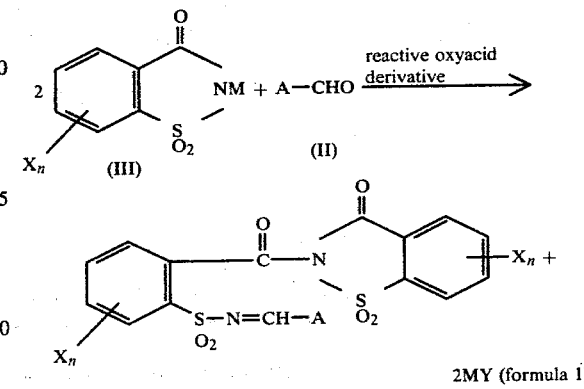

wherein Y represents halogen or a residue resulting from the removal of a dissociable hydrogen atom from the oxyacid.

This reaction is generally carried out in an organic solvent or using an excessive amount of the compound of general formula (II) which serves concurrently as a solvent. It is convenient that the compound of general formula (III) be used in the form of an anhydrous alkali metal salt, an anhydrous alkaline earth metal salt, a tertiary amine salt, etc. Alternatively, the free acid of general formula (III) may be added to the reactant solution, and a suitable base used as a salt-forming reagent, such as a tertiary amine (e.g., triethylamine) or an inorganic base (e.g., an alkali carbonate or an alkali bicarbonate) may be added to form a salt of the compound (III) in situ.

Examples of the reactive derivatives of the oxyacids at the hydroxyl group which can be used for this reaction include acid halides of various oxyacids (such as: phosphorus trichloride, phosphorus tribromide, phosphorus oxychloride, phosphorus oxybromide, phosphorus pentachloride, phosphorus pentabromide, phosphoric ester halides, phosphorous ester halides, phosphonic acid halides, phosphinic acid halides, thionyl chloride, sulfuryl chloride, thionyl bromide, sulfuryl bromide, phosgene, trichloromethyl chloroformate, chlorosulfonic acid, chlorosulfonic acid esters, trimethylchlorosilane, dimethyldichlorosilane, trichloromethylsilane, organic sulfonic acid chlorides, organic sulfinic acid chlorides, organic sulfonic acid chlorides, chloroformates and carboxylic acid chlorides), carboxylic acid anhydrides, acid anhydrides of strong acids such as sulfuric anhydride, sulfonic acid anhydrides, dialkylsulfuric acids, mixed acid anhydrides formed between various organic acids or inorganic acids (such as mixed acid anhydrides formed between carboxylic acids and sulfonic acids, sulfuric acid or carbonic acid), and various active esters (such as active esters of strong acids, e.g., dialkyl sulfates). These are merely exemplary and do not limit the scope of the invention.

One possible reaction mechanism for this reaction is that the active derivative of the oxyacid reacts with the compound of formula (II) to form a formiminium cation of the general formula (IV)

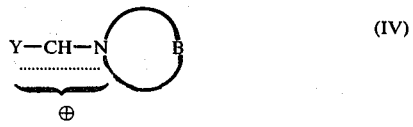

which is very reactive toward a nucleophilic reagent, or to form a very reactive cation of the general formula (V)

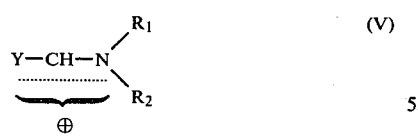

in the intermediate stage, and the cation reacts with the salts of the compound of the general formula (III) to form the stable compound of general formula (I) as a final product.

Generally, the reactive derivative of the oxyacid is used in an amount of 1 to 2 equivalents (calculated as a strong acid formed when the reactive derivative is completely hydrolyzed) to the salt of the compound of general formula (III). A base may be optionally added to neutralize the strong acid formed by the reaction and to make the reaction of the cation of the general formula (IV) or (V) with the salt of saccharin [the compound of general formula (III)] proceed smoothly.

The organic solvent used in this invention is not limited to those exemplified hereinabove, and may be any organic solvent which does not participate in the reaction and which is a relatively good solvent for the starting compounds or the product. For example, dichloromethane, chloroform, carbon tetrachloride, acetone, benzene, toluene, ethyl ether, isopropyl ether, acetonitrile, tetrahydrofuran, and dioxane can be used.

The reaction is generally carried out at a temperature of from $-50°$ C. to $100°$ C., preferably from $-15°$ C. to $30°$ C. Usually, the reaction ends in several tens of minutes to ten or so odd hours. The final product can be easily isolated from the reaction mixture in the customary manner. For example, the solvent may be distilled from the reaction mixture and water added to precipitate the crude product. Or the crude product may be obtained by dissolving the reaction mixture in an organic solvent, separating the product from the inorganic salt, and distilling off the solvent. Recrystallization of the crude product from a suitable solvent can afford a purified product.

The following Examples specifically illustrate the synthesis of the compounds of this invention. It should be understood that these examples should not be construed as limiting the scope of this invention.

SYNTHESIS EXAMPLE 1

Preparation of 2-{2'-[(morpholinomethyleneamino)sulfonyl]-benzoyl}-1,2-benzoisothiazolin-3-one-1,1-dioxide:

N-formylmorpholine (3 ml) and 2.05 g of anhydrous sodium saccharin were added to 10 ml of dichloromethane. The mixture was cooled to $-30°$ C., and with stirring, 1.65 ml (corresponding to about 5 millimoles of phosgene) of a carbon tetrachloride solution containing 30% of phosgene (W/V %) was added. The temperature of the mixture was raised to room temperature over a period of about 1 hour and stirred at room temperature for 2 hours. The solvent was distilled off under reduced pressure. Water was added to the remaining oily product, and under ice cooling, the mixture was stirred until the oily product crystallized. The crystals were collected by filtration, thoroughly washed with water, and dried to afford 1.70 g of white crystals (yield 73.4%), decomposition point:160°–169° C. Recrystallization of the crude crystals from acetone yielded white needle-like crystals having a decomposition point of 173° to 175° C.

NMR spectrum (DMSO-d 6-TSP) δ: 8.55–7.65 (9H, m, aromatic ring and methine protons); 3.575 (broad s); 3.52 (s)

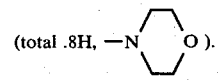

IR spectrum (nujol) cm$^{-1}$ (only main absorption bands other than nujol betweel 3500 and 1400 cm$^{-1}$, and between 1000 and 600 cm$^{-1}$ are described. The description of absorption bands between 1400 and 1000 cm$^{-1}$ are omitted due to its complexity; the same applies to the compounds described hereinbelow.): 3100, 1766, 1706, 1626, 947, 881, 862, 804, 779, 749, 715, 672, 652, 639, 600.

Mass spectrum: Molecular ion peak m+=463 was detected.

Elemental analysis for $C_{19}H_{17}N_3O_7S_2$ (463.49): Calculated (%): C 49.24; H 3.70; N 9.07; S 13.83; Found (%): C 49.42; H 3.75; N 8.79; S 13.70.

SYNTHESIS EXAMPLE 2

N-formylmorpholine (6 ml) and 4.2 g of anhydrous sodium saccharin were added to 20 ml of dichloromethane. The mixture was cooled to −40° C., and with stirring, 1.2 g of thionyl chloride was added. The mixture was worked up in the same way as in Synthesis Example 1 to afford 3.54 g of white crystals (yield 76.4%). The product showed the same IR and NMR spectra as those of the compound obtained in Synthesis Example 1.

SYNTHESIS EXAMPLE 3

N-formylmorpholine (11.5 g) and 20.5 g of anhydrous sodium saccharin were added to 50 ml of dichloromethane. The mixture was cooled to 3° C., and with stirring, 5.2 g of phosphorus oxychloride was added, whereupon the inside temperature rose to 6° C. The mixture was stirred at room temperature for 2 hours, and then worked up in the same way as in Synthesis Example 1 to afford 13.17 g (56.8%) of white crystals. The IR and NMR spectra of this product were identical to those of the compound obtained in Synthesis Example 1.

SYNTHESIS EXAMPLE 4

N-formylmorpholine (6 ml), 3.66 g of anhydrous saccharin and 2.02 g of triethylamine were added to 20 ml of dichloromethane. The mixture was cooled to −20° C., and with stirring, 1.81 g of phosphorus tribromide was added. The mixture was worked up in the same way as in Synthesis Example 1 to afford 2.6 g (56.1%) of white crystals. The IR and NMR spectra of this product were identical to those of the compound of Synthesis Example 1.

SYNTHESIS EXAMPLE 5

Preparation of 2-{4'-chloro-2'-[(morpholinomethyleneamio)-sulfonyl]-benzoyl}-6-chloro-1,2-benzoisothiazolin-3-one-1,1-dioxide:

N-formylmorpholine (10 ml), 2.39 g of 6-chlorosaccharin and 1.01 g of triethylamine were added to 10 ml of dichloromethane. The mixture was cooled to −40° C., and with stirring, 0.6 g of thionyl chloride was added. The temperature of the mixture was raised to 0° C. over about 1 hour, and then the mixture was stirred at room temperature for 3 hours.

Dichloromethane was distilled off, and 80 ml of ice water was added to the remaining oily product. The precipitated white crystals were washed with methanol, and dried to afford 1.25 g of white crystals. Decomposition point: 201°–203° C. Recrystallization from acetone yielded white crystals having a decomposition point of 206° to 208° C.

NMR spectrum (DMSO-d6-TSP) δ: 8.80–7.63 (7H, m, aromatic ring and methine protons); 3.64 (broad s) and 3.57 (s)

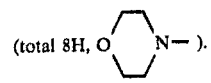

(total 8H, O N— ).

IR spectrum (nujol) cm$^{-1}$: 3100, 1764, 1709, 1624, 1589, 949, 882, 864, 838, 800, 862, 727, 676, 667, 640, 604.

Elemental analysis for $C_{19}H_{15}N_3O_7S_2Cl$ (533.37): Calculated (%): C 42.79; H 2.83; N 7.88. Found (%): C 42.98; H 2.76; N 7.93.

SYNTHESIS EXAMPLE 6

Preparation of 2-{4'-nitro-2'-[(morpholinomethyleneamino)-sulfonyl]-benzoyl}-6-nitro-1,2-benzoisothiazolin-3-one-1,1-dioxide:

To 3 ml of dichloromethane were added 300 mg of 6-nitrosaccharin (m.p. 204°–205° C.), 1 ml of N-formylmorpholine and 135 mg of triethylamine. The mixture was cooled to −30° C., and with stirring, 79 mg of thionyl chloride was added. The mixture was worked up in the same way as in Synthesis Example 1 to afford 241 mg of light yellow crystals having a decomposition point of 129° to 132° C. Recrystallization from acetone afforded crystals having a decomposition point of 139° to 140° C.

NMR spectrum (DMSO-d6-TSP) δ: 8.88–8.07 (7H, m, aromatic ring and methine protons); 3.70–3.28

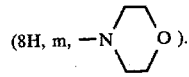

(8H, m, —N O ).

IR spectrum (nujol) cm$^{-1}$: 3075, 1739, 1613, 1538, 1440, 913, 892, 862, 811, 781, 739, 718, 669, 662, 634.

Elemental analysis for $C_{19}H_{15}N_5O_{11}S_2$ (553.49) Calculated (%): C 41.23; H 2.73; N 12.65. Found (%): C 41.54; H 3.40; N 12.58.

SYNTHESIS EXAMPLE 7

Preparation of 2-{2'-[(dimethylaminomethyleneamino)-sulfonyl]benzoyl}-1,2-benzoisothiazolin-3-one-1,1-dioxide:

Anhydrous sodium saccharin (4.2 g) and 6.5 ml of dimethylformamide were added to 22 ml of dichloromethane. The mixture was cooled to −20° C., and with stirring, 1.19 g of thionyl chloride was added. The temperature of the mixture was raised to room temperature over the period of about 1 hour, and the mixture was then stirred at room temperature for 1 hour. The dichloromethane was distilled off, and 100 ml of ice water was added to the residue. The mixture was stirred, and the precipitated crystals were collected by filtration, washed with water, and dried to yield 3.64 g (86.4%) of white crystals having a decomposition point of 169° to 173° C. Recrystallization from acetone afforded needle-like crystals having a decomposition point of 183° to 185° C.

NMR spectrum (DMSO-d6-TSP) δ: 8.54–7.69 (9H, m, aromatic ring and methine protons); 3.12 (3H, s, —CH$_3$); 2.90 (3H, s, —CH$_3$).

IR spectrum (nujol) cm$^{-1}$: 3100, 1766, 1706, 1626, 947, 881, 862, 804, 779, 749, 715, 672, 652, 639, 600.

Mass spectrum: molecular ion peak M+=421 was detected.

Elemental analysis for $C_{17}H_{15}N_3O_6S_2$ (421.45) Calculated (%): C 48.45; H 3.59; N 9.97; S 15.21. Found (%): C 48.31; H 3.60; N 9.83; S 15.18.

SYNTHESIS EXAMPLE 8

Anhydrous sodium saccharin (10.25 g) and 25 ml of dimethylformamide were added to 25 ml of dichloromethane, and with stirring at −15° C., 2.55 g of phosphorus oxychloride was added. The mixture was worked up in the same way as in Synthesis Example 7 to yield 10.1 g of white crystals. The IR and NMR spectra of this product were identical to those of the compound obtained in Synthesis Example 7.

SYNTHESIS EXAMPLE 9

Anhydrous sodium saccharin (2.05 g) and 3 ml of dimethylformamide were added to 10 ml of dichloromethane, and the mixture was cooled to −40° C., and with stirring, 1.65 ml (corresponding to 5 millimoles of phosgene) of a carbon tetrachloride solution containing 30% of phosgene (W/V %) was added. The mixture was worked up in the same way as in Synthesis Example 7 to afford 1.76 g (83.5%) of white crystals. The NMR and IR spectra of this product were identical to those of the compound obtained in Synthesis Example 7.

SYNTHESIS EXAMPLE 10

Anhydrous sodium saccharin (4.1 g) and 8 ml of dimethylformamide were added to 8 ml of dichloromethane, and the mixture was cooled to −30° C. With stirring, 915 mg of phosphorus trichloride was added, and subsequently, the mixture was worked up in the same way as in Synthesis Example 7 to yield 3.65 g (86.7%) of white crystals. The IR and NMR spectra of this product were identical to those of the compound obtained in Synthesis Example 7.

SYNTHESIS EXAMPLE 11

Anhydrous sodium saccharin (2.05 g) and 6 ml of dimethylformamide were added to 5 ml of dichloromethane, and the mixture was cooled to −50° C. With stirring, 416 mg of phosphorus pentachloride was added, and the mixture was worked up in the same way as in Synthesis Example 7 to yield 3.15 g (74.7%) of white crystals. The IR and NMR spectra of this product were identical to those of the compound obtained in Synthesis Example 7.

SYNTHESIS EXAMPLE 12

Preparation of 2-{2'-[(diethylaminomethyleneamino)sulfonyl]-benzoyl}-1,2-benzoisothiazolin-3-one-1,1-dioxide Anhydrous sodium saccharin (4.2 g) was added to 12 ml of diethylformamide, and the mixture was cooled to −40° C. With stirring, 1.18 g of thionyl chloride was added. The mixture was worked up in the same way as in Synthesis Example 7 to yield 4.0 g (89.3%) of white crystals having a decomposition point of 186° to 187° C. Recrystallization from acetone yielded a pure product having a decomposition point of 194° to 195° C.

NMR (DMSO-d6-TSP) δ: 8.47–7.67 (9H, m, aromatic ring and methine protons); 3.36 (2H, q, J=7 Hz, —C$\underline{H_2}$—CH₃); 3.43 (2H, q, J=7 Hz, —C$\underline{H_2}$—CH₃); 1.18 (3H, t, J=7 Hz, —CH₂—C$\underline{H_3}$); 1.02 (3H, t, J=7 Hz, —CH₂—C$\underline{H_3}$).

IR spectrum (nujol) cm⁻¹: 3100, 1765, 1712, 1628, 957, 884, 816, 792, 773, 754, 738, 716, 676, 648, 606.

Elemental analysis for $C_{19}H_{19}N_3O_6S_2$ (449.50) Calculated (%): C 50.77; H 4.26; N 9.35. Found (%): C 49.02; H 4.12; N 8.90.

SYNTHESIS EXAMPLE 13

Preparation of 2-{4'-chloro-2'-[(dimethylaminomethyleneamino)sulfonyl]benzoyl}-6-chloro-1,2-benzoisothiazolin-3-one-1,1-dioxide To 12 ml of dimethylformamide were added 2.39 g of 6-chlorosaccharin (m.p. 216°–218° C.) and 1.01 g of triethylamine, and the mixture was cooled to −50° C. With stirring, 0.6 g of thionyl chloride was added. The mixture was worked up in the same way as in Synthesis Example 7 to yield a white precipitate. The precipitate was filtered, washed with cold methanol, and dried to afford 1.92 g of white crystals having a decomposition point of 198° to 199° C. Recrystallization from acetone afforded crystals having a decomposition point of 201° to 202° C.

NMR spectrum (DMSO-d6-TSP) δ: 8.80–7.63 (7H, m, aromatic ring and methine protons); 3.12 (3H, s, —CH₃); 2.90 (3H, s, —CH₃).

IR spectrum (nujol) cm⁻¹: 3100, 3070, 1758, 1712, 1632, 1589, 1432, 912, 860, 832, 764, 732, 674, 616.

Elemental analysis for $C_{17}H_{13}N_3O_6S_2Cl_2$ (490.33). Calculated (%): C 41.64; H 2.67; N 8.57. Found (%): C 41.64; H 2.57; N 8.59.

SYNTHESIS EXAMPLE 14

Preparation of 2-{4'-chloro-2'-[(diethylaminomethyleneamino)sulfonyl]benzoyl}-6-chloro-1,2-benzoisothiazolin-3-one-1,1-dioxide To a mixture of 10 ml of dichloromethane and 10 ml of diethylformamide were added 2.39 g of 6-chlorosaccharin and 1.01 g of triethylamine, and the mixture was cooled to −40° C. With stirring, 0.6 g of thionyl chloride was added, and the temperature of the mixture was raised to room temperature over the course of about 1 hour. The mixture was then stirred at room temperature for 6 hours. The dichloromethane was distilled off, and 80 ml of ice water was added. The precipitated gummy material was collected by decantation, and 30 ml of methanol was added. When the mixture was stirred, it gradually became a uniform slurry. The slurry was filtered, washed with cold methanol, and dried to yield 1.64 g of white crystals having a decomposition point of 195° to 197° C. Recrystallization from acetone yielded a purified product having a decomposition point of 199° to 202° C.

NMR spectrum (DMSO-d6-TSP) δ: 8.80–7.63 (7H, m, aromatic ring proton and methine protons); 3.49 (2H, q, J=7 Hz, —CH₂—CH₃); 3.38 (2H, q, J=7 Hz,—C$\underline{H_2}$—CH₃); 1.20 (3H, t, —CH₂—C$\underline{H_3}$); 1,04 (3H, t,—CH₂—C$\underline{H_3}$).

IR spectrum (nujol) cm⁻¹: 3084, 1760, 1715, 1621, 1588, 1451, 991, 959, 935, 889, 854, 832, 775, 765, 745, 729, 675, 615.

Elemental analysis for $C_{19}H_{17}N_3O_6S_2Cl_2$ (518.38). Calculated (%): C 44.02; H 3.30; N 8.11. Found (%): C 43.75; H 2.97; N 7.88.

SYNTHESIS EXAMPLE 15

Preparation of
2-{2'-[(N-methyl-N-phenylaminomethyleneamino)sulfonyl]benzoyl}-1,2-benzoisothiazolin-3-one-1,1-dioxide Anhydrous sodium saccharin (4.2 g) was added to a mixture of 8 ml of dichloromethane and 8 ml of N-formyl-N-methylaniline, and the mixture was cooled to −40° C. With stirring, 1.3 g of thionyl chloride was added. The temperature of the mixture was raised to room temperature over the course of about 1 hour, and then the mixture was stirred at room temperature for 3 hours. The dichloromethane was distilled off, and the resulting oily product was washed with water, and methanol was added. When the mixture was stirred, crystals were formed. The crystals were collected by filtration, washed thoroughly with methanol and dried to yield 3.1 g of white crystals having a decomposition point of 188° to 190° C. Recrystallization from acetone yielded a pure product having a decomposition point of 208° to 210° C.

NMR spectrum (DMSO-d6-TSP) δ: 8.33–7.40 (14H, m, aromatic ring and methine protons); 3.39 (3H, s, —CH$_3$).

IR spectrum (nujol) cm$^{-1}$: 3080, 1766, 1718, 1700, 1607, 1580, 1499, 1417, 897, 817, 779, 746, 715, 705, 694, 672, 653, 634.

Elemental analysis for $C_{22}H_{17}N_3O_6S_2$ (483.51). Calculated (%): C 54.65; H 3.54; N 8.69. Found (%): C 53.42; H 3.43; N 8.47.

SYNTHESIS EXAMPLE 16

Preparation of
2-{4'-chloro-2'-[(N-methyl-N-phenylaminomethyleneamino)sulfonyl]benzoyl}-6-chloro-1,2-benzoisothiazolin-3-one-1,1-dioxide To a mixture of 5 ml of dichloromethane and 3 ml of N-formyl-N-methylaniline were added 2.1 g of 6-chlorosaccharin and 880 mg of triethylamine, and the mixture was cooled to −40° C. With stirring, 572 mg of thionyl chloride was added. The temperature of the mixture was raised to room temperature over the course of about 1 hour, and the mixture was stirred at room temperature for 2 hours. The mixture was subsequently worked up in the same way as in Synthesis Example 15 to yield 1.28 g of white crystals having a decomposition point of 194° to 196° C. Recrystallization from acetone yielded a pure product having a decomposition point of 204° to 207° C.

NMR spectrum (DMSO-d6-TSP) δ: 8.78–7.38 (12H, m, aromatic ring and methine protons); 3.38 (3H, s, —CH$_3$).

IR spectrum (nujol) cm$^{-1}$: 3100, 1770, 1711, 1607, 1577, 1498, 901, 859, 834, 776, 765, 725, 698, 678, 665, 638, 602.

Elemental analysis for $C_{22}H_{15}N_3O_6S_2Cl_2$ (552.39). Calculated (%): C 47.84; H 2.74; N 7.61. Found (%): C 47.58; H 2.63; N 7.64.

SYNTHESIS EXAMPLE 17

Preparation of
2-{4'-nitro-2'-[(dimethylaminomethyleneamino)sulfonyl]benzoyl}-6-nitro-1,2-benziosthiazolin-3-one-1,1-dioxide To a mixture of 5 ml of dichloromethane and 4 ml of dimethylformamide were added 1.14 g of 6-nitrosaccharin (m.p. 204°–205° C.) and 505 mg of triethylamine, and the mixture was cooled to −30° C. With stirring, 300 mg of thionyl chloride was added. The temperature of the mixture was raised to 0° C. over the course of 1 hour, and the mixture was stirred at room temperature for 5 hours. The dichloromethane was distilled off, and 50 ml of ice water was added, whereupon white crystals precipitated. The crystals were collected by filtration, thoroughly washed with water, and dried to form 910 mg of slightly light yellow crystals. Recrystallization from acetone yielded slightly light yellow crystals having a decomposition point of 206° to 208° C.

NMR spectrum (DMSO-d6-TSP) δ: 9.45–7.70 (7H, m, aromatic ring and methine protons); 3.14 (3H, s, —CH$_3$); 2.91 (3H, s, —CH$_3$).

IR spectrum (nujol) cm$^{-1}$: 3100, 1763, 1709, 1635, 1536, 1429, 922, 893, 856, 807, 742, 732, 669, 661, 613.

Elemental analysis for $C_{17}H_{13}N_5O_{10}S_2$ (511.45) Calculated (%): C 39.92; H 2.56; N 13.69. Found (%): C 40.16; H 2.58; N 14.14.

Table 1 summarizes the specific examples and properties of the 1,2-benzoisothiazolin-3-one-1,1-dioxides produced by the above methods. The invention, however, is not limited to these specific examples. A, X and n in the table correspond to those given in general formula (I). The numbers of these compounds will be referred to also in Formulation Examples and Test Examples given hereinbelow.

TABLE 1

| Compound No. | A | X | n | Melting Point (decomp.) (°C.) |
|---|---|---|---|---|
| 1 | O(CH$_2$CH$_2$)$_2$N— (morpholino) | H | | 173–175 |
| 2 | O(CH$_2$CH$_2$)$_2$N— | Cl | 1 | 201–203 |
| 3 | O(CH$_2$CH$_2$)$_2$N— | NO$_2$ | 1 | 139–140 |
| 4 | (H$_3$C)$_2$N— | H | | 183–185 |
| 5 | (H$_5$C$_2$)$_2$N— | H | | 194–195 |
| 6 | (H$_3$C)$_2$N— | Cl | 1 | 201–202 |
| 7 | (H$_5$C$_2$)$_2$N— | Cl | 1 | 199–202 |
| 8 | H$_3$C(H$_5$C$_6$)N— | H | | 208–210 |
| 9 | H$_3$C(H$_5$C$_6$)N— | Cl | 1 | 204–207 |

TABLE 1-continued

| Compound No. | A | X | n | Melting Point (decomp.) (°C.) |
|---|---|---|---|---|
| 10 | $H_3C$\N—/$H_3C$ | $NO_2$ | 1 | 206–208 |

The 1,2-benzisothiazolin-3-one-1,1-dioxides of this invention exhibit an antimicrobial activity against a broad range of pathogenic microorganisms on agricultural and horticultural crops, and have an especially superior pesticidal effect against leaf blight and blast on rice and soft rot on Chinese cabbage.

When the compounds of this invention are to be used as agricultural and horticultural pesticides and, especially, antimicrobial agents, they are applied either as such or after dilution with water, a solid powder or other suitable carriers and may optionally be used together with auxiliary agents such as a spreader. They can also be used in the form of various formulations such as a wettable powder, liquid preparation, emulsifiable concentrate, dust or granule prepared by mixing with various liquids or solid carriers and optionally adding auxiliary agents such as a wetting agent, spreader, dispersing agent, emulsifying agent, or sticker by methods generally practiced in the preparation of agricultural chemicals.

In the formulations, liquid carriers may be solvents for the compounds of this invention or liquids which can disperse or dissolve the compounds with the aid of auxiliary agents. Examples of liquid carriers are kerosene, dioxane, acetone, dimethyl sulfoxide, animal and vegetable oils, and surface active agents. Examples of solid carriers are clay, kaolin, talc, diatomaceous earth, silica, calcium carbonate and calcium bicarbonate.

The amounts of the active ingredient and additives can vary over a wide range. When the compound is used in a liquid preparation, a suitable concentration of the compound in the liquid is about 10 ppm to 500 ppm, preferably 100 to 400 ppm. A dust or granular composition desirably contains about 1 to 20%, preferably 3 to 10%, of the compound. When applied to the soil, the compound is desirably used at a rate of about 0.1 to 10 kg, preferably 0.5 to 2.0 kg, per 10 ares.

The compounds of this invention may be used in combination with known pesticides, fungicides, insecticides, herbicides, plant growth regulating agents of fertilizers.

The following Formulation Examples illustrate the use of the 1,2-benzisothiazolin-3-one-1,1-dioxides of this invention as agricultural and horticultural pesticides. It should be understood, however, that these examples do not limit the scope of this invention.

| Formulation Example 1 | |
|---|---|
| Granules: | parts by weight |
| Compound No. 1 | 8 |
| Clay | 89 |
| Carboxymethyl cellulose | 3 |

The above ingredients were mixed, and a suitable amount of water was added. They were kneaded, molded, and dried to form a granular composition. This composition was sprayed in an amount of 3 kg per 10 ares.

| Formulation Example 2 | |
|---|---|
| A Wettable Powder: | parts by weight |
| Compound No. 2 | 20 |
| Clay | 10 |
| Diatomaceous earth | 65 |
| Ligninsulfonic acid | 3 |
| Polyoxyethylene alkylaryl ether | 2 |

These ingredients were uniformly mixed and pulverized to form a wettable powder. The wettable powder in a specified concentration was sprayed at a rate of 100 to 150 liters per 10 ares.

| Formulation Example 3 | |
|---|---|
| A Dust: | parts by weight |
| Compound No. 3 | 3 |
| Calcium stearate | 1 |
| Silicic anhydride powder | 1 |
| Clay | 48 |
| Talc | 47 |

These ingredients were pulverized and mixed to form a dust. The dust was sprayed at a rate of 4 kg per 10 ares.

| Formulation Example 4 | |
|---|---|
| Granules: | parts by weight |
| Compound No. 4 | 8 |
| Clay | 89 |
| Carboxymethyl cellulose | 3 |

The above ingredients were mixed, and kneaded with the addition of a suitable amount of water. The mixture was molded, and dried. The resulting granular composition was sprayed at a rate of 3 kg per 10 ares.

| Formulation Example 5 | |
|---|---|
| A Wettable Powder: | parts by weight |
| Compound No. 5 | 20 |
| Clay | 10 |
| Diatomaceous earth | 65 |
| Ligninsulfonic acid | 3 |
| Polyoxyethylene alkylaryl ether | 2 |

The above ingredients were uniformly mixed and pulverized to form a wettable powder. The wettable powder in a predetermined concentration was applied at a rate of 100 to 150 liters per 10 ares.

| Formulation Example 6 | |
|---|---|
| A Dust: | parts by weight |
| Compound No. 10 | 3 |
| Calcium stearate | 1 |
| Silicic anhydride powder | 1 |
| Clay | 48 |
| Talc | 47 |

The above ingredients were mixed and pulverized to form a dust. The dust was sprayed at a rate of 4 kg per 10 ares.

The following Test Examples show the superior efficacy of the compounds of this invention as pesticidal agents against plant pathogens in horticultural and agricultral use.

TEST EXAMPLE 1

Test for controlling leaf blight on rice (submerged application)

Eight parts of each of the compounds shown in Table 1, 89 parts of clay and 3 parts of carboxymethyl cellulose were pulverized and mixed, and kneaded with a suitable amount of water. The mixture was molded, and dried to form a granular composition containing 8% of the active ingredient.

Rice plants were cultivated in pots (1/5,000 are), and immediately before they came into ears, each granular composition was applied at a specified rate to the water in the pots. Bacterium causing leaf blight to rice were inoculated by a single needle method in an amount of $10^8$ cells/ml of the bacterial suspension after a lapse of 10 days from the application of the granular composition. The lengths of lesions in a total of 50 inoculated leaves in three pots in each lot were measured 10 days after the inoculation. Protective values were calculated in accordance with the following equation. Phytotoxicity was simultaneously examined.

$$\text{Protective Value (\%)} = \left(1 - \frac{\text{Average length of lesion in a treated lot}}{\text{Average length of lesion in the untreated lot}}\right) \times 100$$

The results of the tests are shown in Table 2.

TABLE 2

Test for controlling leaf blight of rice (submerged application)

| Compound No. | Dosage (kg/10 ares) | Protective Value (%) | Phytotoxicity |
| --- | --- | --- | --- |
| 1 | 3 | 97 | none |
| 2 | " | 98 | " |
| 3 | " | 95 | " |
| 4 | " | 97 | " |
| 5 | " | 99 | " |
| 6 | " | 89 | " |
| 7 | " | 91 | " |
| 8 | " | 90 | " |
| 9 | " | 88 | " |
| 10 | " | 91 | " |
| Oryzemate (control)* | " | 80 | " |
| Standard non-treated lot | 0 | 0 | " |

*The control agent (Oryzemate: produced by Meiji Seika Kaisha Ltd.) is a commercially available composition containing 8% of 3-allyloxy-1,2-benzisothiazole-1,1-dioxide.

TEST EXAMPLE 2

Test for controlling leaf blight on rice (spraying)

A dust containing 3% of the active ingredient was prepared from 3 parts of each of the compounds shown in Table 1 and 97 parts of talc. Rice plants were cultivated in pots (1/5,000 ares), and immediately before they came into ears, each dust was sprayed in a specified dosage. Fungi of leaf blight of rice were inoculated by a single needle in an amount of $10^8$ cells/ml of the fungus suspension on the date of spraying.

The lengths of lesions in a toal of 50 inoculated leaves in three pots in each lot were measured on the 10th day after the inoculation, the protective values were calculated in accordance with the equation described in Test Example 1. Phytotoxicity was examined at the same time. The results are shown in Table 3.

TABLE 3

Test for controlling leaf blight of rice (foliar spray)

| Compound No. | Dosage (kg/10 ares) | Protective Value (%) | Phytotoxicity |
| --- | --- | --- | --- |
| 1 | 4 | 81 | none |
| 2 | " | 83 | " |
| 3 | " | 85 | " |
| 4 | " | 90 | " |
| 5 | " | 88 | " |
| 6 | " | 81 | " |
| 7 | " | 79 | " |
| 8 | " | 82 | " |
| 9 | " | 81 | " |
| 10 | " | 80 | " |
| Organo-nickel agent (control)* | " | 60 | " |
| Standard non-treated lot | 0 | 0 | " |

*The control agent (Sankeru: produced by Mikasa Chemical Co.) is a commercially available composition containing 6% of nickel dimethyldithiocarbamate.

TEST EXAMPLE 3

Test for controlling blast of rice 10 parts of each of the compounds shown in Table 1, 87 parts of clay and 3 parts of carboxymethyl cellulose were pulverized and mixed, and a suitable amount of water was added. They were kneaded, molded, and dried to form a granular composition containing 10% of the active ingredient.

Rice plants were cultivated in pots (1/5,000 ares), and in the 6-leaf stage, and each granular composition was applied to the soil surface in each pot in a predetermined dosage. One week after the application, a conidia suspension of fungi of rice blast was uniformly sprayed onto the rice plants, and allowed to stand over night in a moisture chamber at 24° C. to cause the rice to be infested by blast. Then, the pots were placed in a greenhouse to develop the disease.

Seven days after the inoculation, the number of lesions was counted, and protective values were calculated in accordance with the following equation.

$$\text{Protective value (\%)} = \left(1 - \frac{\text{Average number of lesions in a treated lot}}{\text{Average number of lesions in the non-treated lot}}\right) \times 100$$

The results of the test are shown in Table 4.

TABLE 4

Test for controlling rice blast

| Compound No. | Dosage (kg/10 ares) | Protective Value (%) | Phytotoxicity |
| --- | --- | --- | --- |
| 1 | 4 | 99 | none |
| 2 | " | 95 | " |
| 3 | " | 96 | " |
| 4 | " | 98 | " |
| 5 | " | 99 | " |
| 6 | " | 82 | " |
| 7 | " | 80 | " |
| 8 | " | 81 | " |
| 9 | " | 79 | " |
| 10 | " | 83 | " |
| Kitazin P (control)* | " | 70 | " |

TABLE 4-continued

| | Test for controlling rice blast | | |
|---|---|---|---|
| Compound No. | Dosage (kg/10 ares) | Protective Value (%) | Phytotoxicity |
| granules | | | |
| Standard non-treated lot | 0 | 0 | " |

*The control agent (Kitazin P; produced by Kumiai Chemical Industry Co., Ltd.) is a commercially available composition containing 17% of O,O-diisopropyl-S-benzyl-thiophosphate.

TEST EXAMPLE 4

Test for controlling rice blast (foliar spraying)

Four-leaf stage rice seedlings grown in plastic pots having a diameter of 6.5 cm (8 seedlings per pot) were used. A test chemical was prepared by diluting each of the compounds shown in Table 1 to predetermined concentrations. The chemical was sprayed by means of a spray gun at a rate of 35 ml per three pots. The treated pots were dried in the air, and placed in a humidity chamber at 24° C. A conidia suspension of blast fungi was uniformly sprayed onto the seedlings, and the seedlings were maintained overnight in the moisture chamber. Then, the pots were transferred into a green house to develop the blast. Seven days after the inoculation, the number of lesions was counted, and protective values were calculated in accordance with the equation shown in Test Example 3. The results of the test are shown in Table 5.

TABLe 5

| | Test for controlling rice blast | | |
|---|---|---|---|
| Compound No. | Concentration of the Active Compound (ppm) | Protective Value (%) | Phytotoxicity |
| 1 | 200 | 100 | none |
| 2 | " | 99 | " |
| 3 | " | 99 | " |
| 4 | " | 99 | " |
| 5 | " | 97 | " |
| 6 | " | 95 | " |
| 7 | " | 90 | " |
| 8 | " | 91 | " |
| 9 | " | 93 | " |
| 10 | " | 93 | " |
| Hinozan emulsifiable concentrate 30 (control)* | 300 | 88 | " |
| Standard non-treated lot | 0 | 0 | " |

*The control agent (Hinozan emulsifiable concentrate 30; produced by Nihon Tokushu Noyaku Seizo K.K.) is a commercially available composition containing 30% of O-ethyl-S,S-diphenylthiophosphate.

TEST EXAMPLE 5

Test for controlling soft rot of Chinese cabbage:

In a field where soft rot of Chinese cabbage occurred frequently, rot-susceptible Chinese cabbage (variety: Matsushima No. 1) was seeded and cultivated. Three test lots each having an area of 10 m² were prepared, and 25 cabbage plants were grown in each lot. Each of the compounds shown in Table 1 was dissolved in a small amount of an organic solvent and then suspended in water to form a chemical having a predetermined concentration. The chemical was sprayed three times at an interval of one week beginning on the seventh day after soft rot occurred for the first time. The total rate of application was 390 liters per 10 ares.

The disease and phytotoxicity were examined 14 days after the final spraying, and the number of plants in which softening occurred in the outer lower leaves was counted, and protective values were calculated by the equation given below. Phytotoxicity was examined at the same time.

The results of the test are shown in Table 6.

$$\text{Protective Value (\%)} = \left(1 - \frac{\text{Average number of diseased plants in a treated lot}}{\text{Average number of diseased plants in the non-treated lot}}\right) \times 100$$

TABLE 6

| | Test for controlling soft rot of Chinese cabbage | | |
|---|---|---|---|
| Compound No. | Concentration of the Active Compound (ppm) | Protective Value (%) | Phytotoxicity |
| 1 | 200 | 81 | none |
| 2 | " | 80 | " |
| 3 | " | 89 | " |
| 4 | " | 94 | " |
| 5 | " | 90 | " |
| 6 | " | 80 | " |
| 7 | " | 83 | " |
| 8 | " | 89 | " |
| 9 | " | 79 | " |
| 10 | " | 85 | " |
| Bordeaux Mixture (Control)* | diluted to 800-fold | 53 | " |
| Standard non-treated lot | 0 | 0 | " |

*The control agent (Bordeaux mixture; produced by Hakko Chemical Co., Ltd.) is a commercially available agent containing 84.1% (50% as copper) of basic copper chloride.

What is claimed is:

1. A compound of the formula (I):

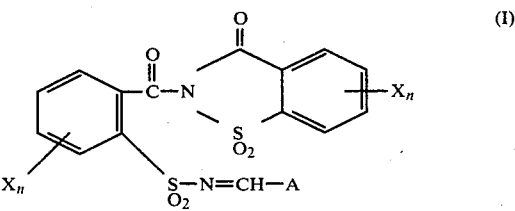

wherein A represents

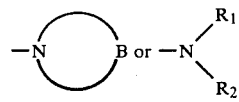

in which B represents a ring-forming residue of a 5- or 6-membered carbon-containing heterocyclic ring containing at least one nitrogen atom and which may further contain an oxygen atom in the ring selected from the group consisting of a morpholine ring, a piperidine ring and a pyrrolidine ring, and $R_1$ and $R_2$ are the same or different and each represents an alkyl group having from 1 to 6 carbon atoms, a phenyl group, a phenyl group substituted with an alkyl or alkoxy group having 1 to 4 carbon atoms or a halogen atom, a benzyl group or a benzyl group substituted with an alkyl or alkoxy group having from 1 to 4 carbon atoms or a halogen atom; n represents 0 or an integer of 1 or 2 corresponding to the number of X substituents; and X represents a halogen atom, a nitro group, a carboxyl group or a carbamoyl group, and when two X substituents are present they may be the same or different.

2. A pesticidal composition comprising as an active ingredient a compound of the formula (I):

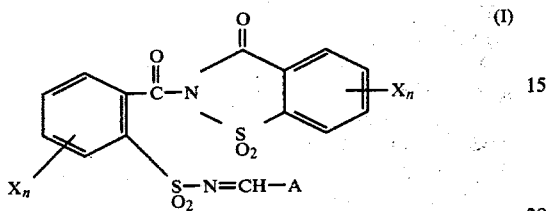  (I)

wherein A represents

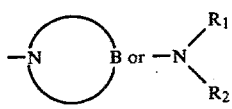

in which B represents a ring-forming residue of a 5- or 6-membered carbon-containing heterocyclic ring containing at least one nitrogen atom and which may further contain an oxygen atom in the ring selected from the group consisting of a morpholine ring, a piperidine ring and a pyrrolidine ring, and $R_1$ and $R_2$ are the same or different and each represents an alkyl group having from 1 to 6 carbon atoms, a phenyl group, a phenyl group substituted with an alkyl or alkoxy group having 1 to 4 carbon atoms or a halogen atom, a benzyl group or a benzyl group substituted with an alkyl or alkoxy group having from 1 to 4 carbon atoms or a halogen atom; n represents 0 or an integer of 1 or 2 corresponding to the number of X substituents; and X represents a halogen atom, a nitro group, a carboxyl group or a carbamoyl group, and when two X substituents are present they may be the same or different, along with a carrier or diluent.

3. The composition of claim 2, wherein a conventional solid or liquid carrier is present.

4. The composition of claim 2, wherein said composition is a powder.

5. The composition of claim 2, wherein said composition is a liquid preparation.

6. The composition of claim 5, wherein said liquid preparation contains about 10 to 500 ppm of said compound.

7. The composition of claim 2, wherein said composition is an emulsifiable concentrate.

8. The composition of claim 2, wherein said composition is a dust or granule composition.

9. The composition of claim 8, wherein said compound is present in an amount of 1 to 20 weight %.

10. A process for controlling pathogenic plant fungi and bacteria which comprises applying to a plant or soil a composition containing a compound of the formula (I) in an amount sufficient to prevent fungal or bacterial growth.

11. A process for preparing a compound of general formula (I):

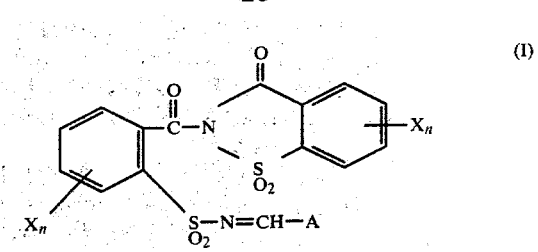  (I)

wherein A represents

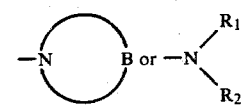

in which B represents a ring-forming residue of a 5- or 6-membered carbon-containing heterocyclic ring containing at least one nitrogen atom and which may further contain an oxygen atom in the ring selected from the group consisting of a morpholine ring, a piperidine ring and a pyrrolidine ring, and $R_1$ and $R_2$ are the same or different and each represents an alkyl group having from 1 to 6 carbon atoms, a phenyl group, a phenyl group substituted with an alkyl or alkoxy group having 1 to 4 carbon atoms or a halogen atom, a benzyl group or a benzyl group substituted with an alkyl or alkoxy group having from 1 to 4 carbon atoms or a halogen atom; n represents 0 or an integer of 1 or 2 corresponding to the number of X substituents; and X represents a halogen atom, a nitro group, a carboxyl group or a carbamoyl group, and when two X substituents are present they may be the same or different, which comprises reacting a compound of general formula (II):

A—CHO  (II)

wherein A is as defined above, with a compound of general formula (III) or a salt thereof

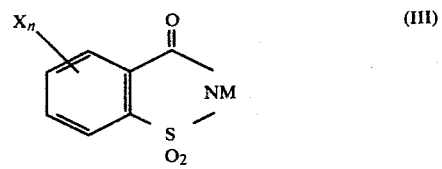  (III)

wherein n and X are defined above, and M represents a hydrogen atom or a monovalent cation, in the presence of a reactive derivative of an oxyacid at its hydroxyl group, said reactive derivative of an oxyacid being selected from the group consisting of acid halides of oxyacids, carboxylic acid anhydrides, acid anhydrides of strong acids, mixed acid anhydrides formed between organic acids or inorganic acids, and active esters.

12. A compound as in claim 1 wherein $R_1$ and $R_2$ are the same or different and each represents a straight or branched chain alkyl group having from 1 to 6 carbon atoms, a phenyl group, a phenyl group substituted with an alkyl group having from 1 to 4 carbon atoms or a halogen atom, a benzyl group, or a benzyl group substituted with an alkyl group having from 1 to 4 carbon atoms or a halogen atom.

13. A pesticidal composition as in claim 2 wherein $R_1$ and $R_2$ are the same or different and each represents a straight or branched chain alkyl group having from 1 to 6 carbon atoms, a phenyl group, a phenyl group substituted with an alkyl group having from 1 to 4 carbon atoms or a halogen atom, a benzyl group, or a benzyl group substituted with an alkyl group having from 1 to 4 carbon atoms or a halogen atom.

14. A process as in claim 11 wherein $R_1$ and $R_2$ are the same or different and each represents a straight or branched chain alkyl group having from 1 to 6 carbon atoms, a phenyl group, a phenyl group substituted with an alkyl group having from 1 to 4 carbon atoms or a halogen atom, a benzyl group, or a benzyl group substituted with an alkyl group having from 1 to 4 carbon atoms or a halogen atom.

15. A compound as in claim 12, wherein $R_1$ and $R_2$ are methyl, ethyl, phenyl, or benzyl groups.

16. A pesticidal composition as in claim 13, wherein $R_1$ and $R_2$ are methyl, ethyl, phenyl, or benzyl groups.

17. A process as in claim 14 wherein $R_1$ and $R_2$ are methyl, ethyl, phenyl, or benzyl groups.

18. A compound as in claim 1 wherein the heterocyclic ring is morpholine.

19. A pesticidal composition as in claim 2, wherein the heterocylic ring is morpholine, piperidine, or pyrrolidine.

20. A pesticidal composition as in claim 2, wherein the heterocyclic ring is morpholine.

21. A process as in claim 11, wherein the heterocyclic ring is morpholine.

22. A compound as in claim 1 wherein n is 0 or 1.

23. A pesticidal composition as in claim 2 wherein n is 0, 1, or 2.

24. A pesticidal composition as in claim 2 wherein n is 0 or 1.

25. A process as in claim 11, wherein n is 0 or 1.

26. A process as in claim 11, wherein the reaction is carried out at a temperature from $-50°$ C. to $100°$ C. in a solvent comprising dichloromethane, chloroform, carbon tetrachloride, acetone, benzene, toluene, ethylether, isopropylether, acetonitrile, tetrahydrofuran, or dioxane.

27. A process as in claim 24, wherein the reaction is carried out at a temperature of from $-15°$ C. to $30°$ C.

28. A process as in claim 1, wherein the derivative of the oxyacid is selected from the group consisting of phosphorus trichloride, phosphorus tribromide, phosphorus oxychloride, phosphorus oxybromide, phosphorus pentachloride, phosphorus pentabromide, phosphoric ester halides, phosphorus ester halides, phosphonic acid halides, phosphinic acid halides, thionyl chloride, sulfuryl chloride, thionyl bromide, sulfuryl bromide, phosgene, trichloromethyl chloroformate, chlorosulfinic acid, chlorosulfonic acid esters, trimethylchlorosilane, dimethyldichlorosilane, trichloromethylsilane, organic sulfonic acid chlorides, organic sulfinic acid chlorides, chloroformates and carboxylic acid chlorides, sulfuric anhydride, sulfonic acid anhydrides, dialkylsulfuric acids, mixed acid anhydrides formed between carboxylic acids and sulfonic acids, sulfuric acid, or carbonic acid, and dialkyl sulfates.

* * * * *